(12) United States Patent
Yacyshyn

(10) Patent No.: US 11,173,187 B2
(45) Date of Patent: Nov. 16, 2021

(54) CONCENTRATED OIL-BASED POLYPHENOL COMPOSITION AND A METHOD OF PRODUCING THE OIL-BASED POLYPHENOL COMPOSITION

(71) Applicant: Immortazyme Company Ltd., Calgary (CA)

(72) Inventor: Vincent Yacyshyn, Calgary (CA)

(73) Assignee: IMMORTAZYME COMPANY LTD., Calgary (CA)

(*) Notice: Subject to any disclaimer, the term of this patent is extended or adjusted under 35 U.S.C. 154(b) by 0 days.

(21) Appl. No.: 16/675,428

(22) Filed: Nov. 6, 2019

(65) Prior Publication Data

US 2020/0148971 A1 May 14, 2020

Related U.S. Application Data

(60) Provisional application No. 62/760,697, filed on Nov. 13, 2018.

(51) Int. Cl.
| | | |
|---|---|---|
| *A61K 36/00* | (2006.01) | |
| *C11B 3/00* | (2006.01) | |
| *A61K 36/185* | (2006.01) | |
| *A61K 36/899* | (2006.01) | |
| *C11B 1/10* | (2006.01) | |
| *A23L 33/12* | (2016.01) | |
| *C11B 3/12* | (2006.01) | |

(52) U.S. Cl.
CPC ............ *A61K 36/00* (2013.01); *A61K 36/185* (2013.01); *A61K 36/899* (2013.01); *C11B 3/008* (2013.01); *A23L 33/12* (2016.08); *C11B 1/10* (2013.01); *C11B 3/12* (2013.01)

(58) Field of Classification Search
CPC ......... A23L 33/12; A61K 36/00; A61K 31/05; A61K 31/20; A61K 36/185; A61K 36/899; A61P 7/00
See application file for complete search history.

(56) References Cited

U.S. PATENT DOCUMENTS

| | | | |
|---|---|---|---|
| 4,126,707 A | 11/1978 | Hart | |
| 4,485,016 A | 11/1984 | Hopkins | |
| 5,712,305 A * | 1/1998 | Romanczyk, Jr. .... | A23L 33/105 514/453 |
| 5,871,794 A | 2/1999 | Brito | |
| 6,469,053 B1 * | 10/2002 | Romanczyk, Jr. ... | A61K 9/2068 514/456 |
| 6,537,546 B2 | 3/2003 | Echigo | |
| 6,610,320 B2 * | 8/2003 | Schmitz .................... | A61P 9/02 424/440 |
| 6,900,241 B2 | 5/2005 | Romanczyk | |
| 7,145,031 B1 | 12/2006 | Arcangeli | |
| 7,312,056 B2 | 12/2007 | Saville | |
| 7,387,802 B2 | 6/2008 | Sambanthamurthi | |
| 7,892,805 B2 | 2/2011 | Saville | |
| 8,124,137 B2 * | 2/2012 | Nakamoto ............... | A61K 8/97 424/725 |
| 8,242,130 B2 | 8/2012 | Wong | |
| 8,349,591 B2 | 1/2013 | Desbarats | |
| 8,470,380 B2 | 6/2013 | Wood | |
| 8,741,855 B2 | 6/2014 | Quave | |
| 8,758,832 B1 * | 6/2014 | Anderson ............ | A61K 36/185 424/725 |
| 8,771,764 B2 | 7/2014 | Abeywardena | |
| 8,818,737 B2 | 8/2014 | Yang | |
| 9,125,903 B2 | 9/2015 | Koverech | |
| 9,254,280 B2 | 2/2016 | Cole | |
| 9,283,203 B2 | 3/2016 | French | |
| 9,580,735 B2 | 2/2017 | Fukuura | |
| 9,688,712 B2 | 6/2017 | Yamada | |
| 9,743,679 B2 | 8/2017 | Perez | |
| 9,750,782 B2 | 9/2017 | Abeywardena | |
| 10,071,912 B2 | 9/2018 | Schulte | |
| 10,358,669 B2 | 7/2019 | Desbarats | |
| 2006/0234948 A1 * | 10/2006 | Empie .................. | A61K 31/726 514/22 |
| 2008/0033038 A1 * | 2/2008 | Shytle .................. | A61K 31/353 514/456 |
| 2009/0311397 A1 | 12/2009 | Whalen | |
| 2013/0118590 A1 | 5/2013 | Desbarats | |
| 2016/0298155 A1 | 10/2016 | Desbarats | |
| 2017/0107452 A1 | 3/2017 | Dasari | |

(Continued)

FOREIGN PATENT DOCUMENTS

| | | |
|---|---|---|
| EP | 221959 | 5/1987 |
| WO | 1986/06589 | 11/1986 |

(Continued)

OTHER PUBLICATIONS

Martain et al., Polyphenols as diewtary supplements: a double-edged sword, Nutritional and dietary supplements, Dover press, No. 2, pp. 1-12 (Year: 2010).*
Pandey et al., Plant polyphenols as dietary antioxidants n human health and disease, Oxidative medicine and cellular longevity, vol. 2, issue 5, pp. 270-278 (Year: 2009).*
Kerem.Z Interactions between CYP3A4 and Dietary Polyphenols. Oxidative Medicine and cellular Longevity. vol. 15. Article 854015. pp. 1-15.

(Continued)

*Primary Examiner* — Yate' K Cutliff

(74) *Attorney, Agent, or Firm* — Jeffrey S. Melcher; Melcher Patent Law PLLC

(57) ABSTRACT

Provided is a method for producing a concentrated oil-based polyphenol composition for human consumption. The unique combination of polyphenols in a biologic oil-based formulation may be administered for optimal effects on human platelets, lipids, and inflammatory markers. These physiologic changes have beneficial effects for human health and longevity.

9 Claims, No Drawings

(56) References Cited

U.S. PATENT DOCUMENTS

| | | | |
|---|---|---|---|
| 2017/0239253 A1* | 8/2017 | Zemel | A61K 9/20 |
| 2017/0247721 A1 | 8/2017 | Desbarats | |
| 2018/0140709 A1* | 5/2018 | Chancey | A61K 47/20 |

FOREIGN PATENT DOCUMENTS

| | | |
|---|---|---|
| WO | 2006/113700 | 10/2006 |
| WO | 2010/045168 | 4/2010 |
| WO | 2013/000088 | 1/2013 |
| WO | 2015/066797 | 5/2015 |
| WO | 2016/033680 | 3/2016 |
| WO | 2020/045168 | 3/2020 |

OTHER PUBLICATIONS

Tsao R. Chemistry and Biochemistry of Dietary Polyphenols. Nutrients. Feb. 2010. 1231-1246.

Brudzynski, K et al. Polyphenol—Protein Complexes and Their Consequences for the Redux Activity, Structure, and Function of Honey. Pol. J Food Nutr. Sci. 2015 vol. 65. No. 2 pp. 71-80.

Manach C. et al . Polyphenols: food sources and bioavailability. Am J Clin Nutr. 2004; 79; 727-47.

Scalbert A. et al. Dietary Intake and Bioavailability of Polyphenols. The Journal of Nutrition 130:2073S-2085S, 2000.

Li et al Fish Oil: A Potent Inhibitor of Platelet Adhesiveness. Blood vol. 76, No. 5 (Sep. 1, 1990): pp. 938-945.

Tynkkynen, T. et al. NMR protocol for determination of oxidation susceptibility of serum lipids and application of the protocol to a chocolate study. Metabolomics. Jun. 2012: 8(3); 386-398.

De Sales, P.M. et al. Alpha-Amylase Inhibitors: A Review of Raw Material and Isolated Compounds from Plant Source. J Pharm Pharmaceut Sci 15(1) 141-183, 2012.

Barrett, A. et al. Inhibition of alpha-Amylase and Glucoamylase by Tannins Extracted from Cocoa, Pomegranates, Cranberries, and Grapes. J. Agric. Food Chem. 2013; 61,1477-1486.

Kuksis, A. et al. Composition of molecular distillates of corn oil: isolation and identification of sterol esters. J Lipid Research. vol. 1 No. 4. Jul. 1960. pp. 311-319.

Ximenes et al. 2011. Deactivation of cellulases by phenols. Enzyme and Microbial Technology, vol. 48, pp. 54-60. (Year: 2011).

Zawistoska et al. 1988. Immobilized Metal Affinity Chromatography of Wheat of aamylases. Cereal chemistry, vol. 65, No. 5 , pp. 413-416. (Year: 1988).

Written Opinion issued in PCT/CA2014/000798, dated Mar. 13, 2015, pp. 1-8.

International Search Report issued in PCT/CA2014/000798, dated Mar. 13, 2015, pp. 1-6.

Jonsson, et al. "Biconversion lignocellulose: inhibitors and detoxification," Biotech Biofuels, Jan. 28, 2013, vol. 6(16) pp. 1-10.

Kim, et al., "Soluble inhibitors/deactivators of cellulose enzymes from lignocellulosic biomass," Enzyme Microb. Tech. 2011, vol. 48, pp. 408-415.

Yang, et al., "Enzymatic hydrolysis of cellulosic biomass," Biofuels, 2011, vol. 2(4), pp. 421-450.

Sutton, "A novozymes short report: fermentation inhibitors," Nvozymes, 2011, online, retrieved Mar. 2, 2015, http://bioenergy.novozymes.com/Documents/Ferm_SR_Inhibitors.pdf.

Yennamalli, et al., "Endogluconases: insights into thermostability for biofuel applications," Biotech. Biofuels, Sep. 27, 2013, vol. 6(136), pp. 1-9.

J Agric Food Chemistry 2013, 61, pp. 1477-1486, Barrett "Inhibition of alpha-amalyase . . . ".

J. Am Leather Chem. Assoc 2003, 98, pp. 273-278.

Kulkarni et al., International Journal of Scientific and Research Publications, vol. 3, Issue 4, Apr. 2013.

Howell, "A-type cranberry proanthocyanidins and uropthogenic bacterial anti-adhesion activity," Phytochemistry, 66, pp. 2281-2291.

Ximenes et al.: 'Lignocellulose pretreatment: Beneficial and non-beneficial effects prior to enzyme hydrolysis' [ online], American Chemical Society Meeting Paper, San Diego, Mar. 25, 2012, Retrieved from the Internet: <http://www.purdue.edu/lorre/presentations/Eduardo%20ACS %203 .25 .12.pdf.

International Search Report issued in PCT/CA2015/000482, dated Dec. 21, 2015, pp. 1-2. attached to WO2016/033680.

International Search Report issued in PCT/CA2015/000482, dated Dec. 21, 2015, pp. 1-3.

Written Opinion issued in PCT/CA2015/000482, dated Dec. 21, 2015, pp. 1-6.

International Search Report and Written Opinion issued in PCT/CA2018/050906, dated Oct. 5, 2018, pp. 1-7.

Myburgh, "Polyphenol Supplementation: Benefits for Exercise Performance or Oxidative Stress?" Sports Med (2014) 44 (Suppl 1): S57-S70.

Tejirian, "Inhibition of enzymatic cellulolysis by phenolic compounds", Enzyme Microb Technol. Mar. 7, 2011, 48(3):239-47.

International Search Report issued in PCT/CA2018/050906, dated Oct. 1, 2018, pp. 1-3.

Datta S. et al. Biotech. Feb. 2013;3(1):1-9.

Mukai C. et al. Chem Biol. Sep. 25, 2009: 16(9): 1013-1020.

Ay S.S. et al. International Journal of Scientific and Technological Research vol. 4, No. 6 (2018).

Palazzo G. et al. Sensors and Actuators vol. 202,Oct. 31, 2014, pp. 217-223.

Akkaya A. et al. Journal of Molecular Catalysis. vol 67, Issues 3-4. Dec. 2010. pp. 195-201.

Blanchette C.D. et al. Printable enzyme-embedded materials for methane to methanol conversion. Nat Commun. 2016;7: 11900.

* cited by examiner

CONCENTRATED OIL-BASED POLYPHENOL COMPOSITION AND A METHOD OF PRODUCING THE OIL-BASED POLYPHENOL COMPOSITION

FIELD OF INVENTION

The invention relates to a method of producing and administering polyphenols to mammals, specifically, human beings. The invention also relates a concentrated polyphenol composition.

BACKGROUND OF THE INVENTION

Polyphenols are found in many foods. The total intake of polyphenols is approximately 1 gram per day per individual. However, this estimate is highly variable depending on diet (Finnish 817 mg/individual/day), (Vietnamese 595 mg/individual/day), and (Mediterranean 1.8 g/individual/day). Kerem.Z Interactions between CYP3A4 and Dietary Polyphenols. Oxidative Medicine and cellular Longevity. Vol. 15. Article 854015. Pages 1-15.

Polyphenols are the biggest group of phytochemicals. Polyphenol rich diets have been linked to many health benefits. More than 8000 phenolic structures have been identified. Polyphenols are classified by their source of origin, biological function, and chemical structure. Many different extraction methods are available for the extraction of these polyphenols. Given the hydrophilic nature of these compounds most polyphenols, aglycones, glycosides, and oligomers are extracted using water, polar organic solvents, or mixtures of water. High intake of fruits, vegetables, and whole grains which are rich in polyphenols, has been linked to lowered risks of many chronic diseases including cancer, cardiovascular disease, chronic inflammation, and many degenerative diseases. Tsao R. Chemistry and Biochemistry of Dietary Polyphenols. Nutrients. 2010, 2. 1231-1246.

Polyphenols are believed to act by non-covalently binding between proteins and polyphenols. This interaction involves hydrogen bonds that are formed between electronegative atoms of nitrogen or oxygen, especially of amino (NH2) and hydroxyl (OH) groups and a positively charged hydrogen atom from neighboring hydroxyl or amino groups of another polyphenol or protein molecule. Depending on the polyphenol structure and degree of hydroxylation, the interaction may produce single or multiple hydrogen bonds that influence the strength of the formed complexes. Hydrogen bonds between neighboring protein chains can create bridges that crosslink proteins into aggregates. In addition to hydrogen bonds that involve polar groups, protein and polyphenols may interact by hydrophobic, nonpolar aromatic rings of polyphenols and aromatic amino acids. Brudzynski, K et al. Polyphenol-Protein Complexes and Their Consequences for the Redux Activity, Structure, and Function of Honey. Pol. J Food Nutr. Sci. 2015 Vol. 65. No. 2 pp 71-80.

Polyphenols are abundant micronutrients in our diet. The health benefits of polyphenols depend on the amount consumed and their bioavailability. Intestinal absorption and chemical structure (glycosylation, esterification, and polymerization), food matrix, and excretion influence bioavailability of the various polyphenols. Manach C. et al. Polyphenols: food sources and bioavailability. Am J Clin Nutr. 2004; 79; 727-47.

Dietary polyphenols are present in common fruits, vegetables, and beverages. Phenolic acids account for about one third of the total intake and flavonoids account for the remaining two thirds. The most abundant flavonoids in the diet are flavanols, anthocyanins, and their oxidation products. The main polyphenol dietary sources are fruits and beverages and to a lesser extent vegetables, dry legumes, and cereals. Total intake is approximately one gram per day. Maximum plasma concentrations rarely exceed one micromole after consumption of ten to one-hundred milligrams of a single phenolic compound. The total plasma concentration may be higher and is dependent on the presence of metabolites formed in the body's tissues or by colonic microflora. Scalbert A. et al. Dietary Intake and Bioavailability of Polyphenols. The Journal of Nutrition 130: 2073S-2085S, 2000. I have found that the bioavailability of these polyphenols may be affected by administration of concomitant carbohydrates.

The National Academy of Science Dietary Reference Intakes used to set daily requirements for carbohydrates intakes, estimates adult average daily requirements of at least one hundred grams per day.

Fish oil (the equivalent of six grams of eicosapentaenoic acid per day for twenty-five days) compared with vegetable oil was shown to decrease platelet adhesion to fibrinogen and collagen by sixty percent in eight individuals. The profile of fatty acids extracted from the plasma confirmed the presence of fish oil from the dietary supplements. Li et al Fish Oil: A Potent Inhibitor of Platelet Adhesiveness. Blood Vol 76, No 5 (September 1), 1990: pp 938-945.

Oxidative susceptibility of serum lipids based on proton nuclear magnetic resonance (1H NMR) spectroscopy has been used and compared with spectroscopic measurements. High polyphenol chocolate has been shown to decrease the oxidative susceptibility of serum lipids in addition to significant changes in high-density lipoproteins (HDL), phosphatidylcholine, sphingomyelin, nervonic, docosahexaenoic, and myristic acids. Tynkkynen, T. et al. NMR protocol for determination of oxidation susceptibility of serum lipids and application of the protocol to a chocolate study. Metabolomics. 2012 June: 8(3); 386-398.

Inhibition of alpha-amylase by plant based chemical constituents. Crude extracts and isolated compounds suggest that flavonoids (and in particular hydroxyl groups) are one of the most potent inhibitors of amylase activity. De Sales, P. M. et al. Alpha-Amylase Inhibitors: A Review of Raw Material and Isolated Compounds from Plant Source. J Pharm Pharmaceut Sci 15(1) 141-183, 2012.

A comparison of polyphenols extracted for various food sources has been assessed for inhibition of alpha-amylase and glucoamylase activity. Tannins interact with proteins at their numerous hydroxyl groups. Tannins have been isolated from pomegranate, cranberry, grape, and cocoa. These isolates have been shown to have inhibit alpha-amylase and glucoamylase activities and thermal stability to varying degrees. Barrett, A. et al. Inhibition of alpha-Amylase and Glucoamylase by Tannins Extracted from Cocoa, Pomegranates, Cranberries, and Grapes. J. Agric. Food Chem. 2013; 61, 1477-1486.

It has long been known that molecular distillates of corn oil obtained by solvent and chromatographic extraction contain long chain fatty acid esters, free sterols, sitosterols, and tocopherol esters. Kuksis, A. et al. Composition of molecular distillates of corn oil: isolation and identification of sterol esters. J Lipid Research. Vol. 1 No. 4. July, 1960. PP 311-319

Diet has not been optimized to reduce cardiovascular events due to obesity, glucose intake, and type two diabetes mellitus. Ingestion of polyphenols are unpalatable, noxious, a risk for aspiration or diarrhea, bitter, and anti-aromatic. Gel cap concentrated polyphenols may be absorbed in the small intestine with concentration of the bio-oil to decrease carbohydrate metabolism and the subsequent formation of simple sugars. Prior experience with alteration of polyphenol interaction with commercial enzymes in bio-ethanol plants may provide guidance for this endeavor.

U.S. Pat. No. 9,750,782 describes a composition for improving vascular health using palm oil extract from the palm milling process. The palm oil phenolics are used for treating ventricular tachycardia, peripheral vascular resistance, blood pressure, and cardiovascular health in general. These processes are specific to palm oil and do not teach grain oil or other biologic compounds that may be useful for further phenolic extraction and utilization in an oil based medium for platelet and cardiovascular health mediation.

U.S. Pat. No. 9,688,712 describes a method for producing a polyphenol composition from a hardly water soluble medium by heat treatment in the presence of an aqueous medium. This patent allows hardly water soluble polyphenols to be used in aqueous foods such as soft drinks. Specifically, hesperidin is isolated and used for the enhancement of capillary vessel health, prevention of bleeding, and regulation of blood pressure.

U.S. Pat. No. 9,580,735 describes a method for modifying transcription factors in plants to produce products with elevated levels of antioxidant compounds, including but not limited to flavonols and chlorogenic acid, as well as exhibiting enhanced disease resistance, and optionally altered appearance.

U.S. Pat. No. 9,254,280 describes nutraceutical formulations that improve cognitive function in adults diagnosed with neurodegenerative disease. These foods contain a combination of fisetin (a yellow flavonoid polyphenol) and docosahexaenoic acid (DHA). It is postulated that the unique combination of agents slow the progression of cognitive decline in individuals with neurodegenerative disorders.

U.S. Pat. No. 9,283,203 describes a composition for enhancing cognitive function, increasing blood flow to the brain. These compositions include certain polyphenols such as flavanols, procyanidins, or pharmaceutically acceptable salts or derivatives thereof.

U.S. Pat. No. 7,387,802 describes a process for treatment of oil bearing fruit (oil palm fruit) including the removal of undissolved solids, oleaginous parts, colloids, and higher molecular weight molecules (greater than 41,000 Daltons) from the vegetation liquor to give an aqueous fraction containing the phytochemicals (flavonoids, phenolic acids, and hydroxy acids). Subsequent pH adjustment and aqueous extraction may be used.

U.S. Patent Application Publication No. 2017,0107452 A1 describes products produced from corn oil including free fatty acids. This patent teaches a method for refining corn oil with the capture of free fatty acids. The free fatty acid compound may contain tocopherols of 1 mg/g or less.

U.S. Pat. No. 9,743,679 describes plant extract compositions and methods to isolate monomers, oligomers of cutins for agricultural coatings. The plant extract compositions include fatty acids and fatty acid esters. The cutin layer may contain varying levels of phenolics and anti-oxidants and may lead to varying degrees of resistance of plant species to attack from environmental stressors (water loss, oxidation, mechanical injury, and light) or biotic stressors (fungi, bacteria, viruses and insects etc.).

SUMMARY OF THE INVENTION

Polyphenols are known to have health benefits to mammals, or more specifically human beings. These findings have not been substantiated in various analyses. In part, the complexity of various polyphenols, their respective absorption, and co-factors all play a significant role in the variability of these administered compounds.

The present invention extracts biologic plant-based polyphenols from vegetable, grain, tree, bagasse, or cannabis sources. Conventional extraction methods are utilized to produce an oil-based polyphenol composition. The oil-based polyphenol composition is then concentrated, such as by filtration or fractionation; including, but not limited to, fractional distillation or refining. In this manner, the concentration of high molecular weight polyphenols may be extracted from the oil-based composition to produce a concentrated polyphenol composition. The concentrated polyphenol composition can be encapsulated for administration.

A preferred concentrated polyphenol composition further comprises a carbohydrate. The carbohydrate is preferably at least one oligosaccharide or a polysaccharide.

DETAILED DESCRIPTION OF THE INVENTION

A plant material is harvested and an oil containing polyphenol (oil-based polyphenol composition) is extracted from the plant material using any desired extraction process. For example, the extraction can be conducted by milling and pressing the plant material to extract the oil-based. At least a portion of the oil is then separated from the polyphenols to produce a polyphenol concentrate. Preferably, a high molecular weight polyphenol concentrate is produced, such about 500 to about 4,000 Da. The removal of at least a portion of the oil from the oil-based polyphenol composition can be conducted using any desired method, such as fractional distillation, centrifugation, and/or selective filtration. Since the phenolic concentrate is a food item, preferably food based approved extraction and concentration methods should be utilized. Hazardous and non-food approved solvents should be avoided.

A unique aspect of the present invention allows for the oil-based polyphenol composition to be refined such that the high molecular weight polyphenols can processed, but not limited to the following: be further refined and concentrated by fractional distillation, centrifugation, and/or selective filtration while remaining in their respective oil of origin. The concentration of the refined polyphenols is variable and dependent on the effect derived by administration to a mammal, more specifically a human. An exemplary concentration range is from 500 mg to 3 grams polyphenol(s) in from 0.1 ml to 2 ml oil, preferably, from 0.1 ml to 1.5 ml oil, and more preferably from 0.12 ml to 1.4 ml oil.

The plant material preferably comprises a non-toxic plant, such as vegetable, grain, tree, begasse, or cannabis. The origin of the plant material can be identified by genotype to the polyphenol protein structure.

Any desired amount of carbohydrate may be included. Preferably, when the concentrated polyphenol composition further comprises a carbohydrate, the carbohydrate can be present in an amount of 0.01 g to 400 g per day.

The administered dosage of the concentrated polyphenols can be as desired to provide a desired effect. A non-limiting example of administration amounts is 500 mg per day to 3 grams per day of polyphenol. For example, the amounts can depend on the baseline diet and form of supplementation desired. The desired polyphenol dosage may be delivered in one or a number of acceptable capsules for consumption by the targeted individual. The invention is not bound by the concentration of polyphenols in oil administered. For example, a patient may take 4 capsules of 1.3 ml polyphenol a day, or more or less as desired.

The polyphenol present in the original plant-based oil may be administered depending on the volume of oil and concentration desired. The administered product is subsequently dosed according to the desired effect on platelet structure and function, and/or lipids, and/or inflammatory markers. These changes are surrogate markers for meaningful health related outcomes to the administered organism.

What makes the present invention unique is that:
1) The dosage of polyphenols is specified;
2) The polyphenols are concentrated;
3) The polyphenols remain in the oil of origin;
4) The polyphenols may be combined with a carbohydrate (sugars, oligosaccharides, or polysaccharides); and
5) The outcomes are pre-specified and include individual or combinations of the outcomes.

EXAMPLE

Prior experience with enzymatic reduction in corn ethanol plants by utilizing phenol reduction has provided a wealth of knowledge regarding carbohydrate metabolism. Evaluation has shown gas chromatography/mass spectroscopy absolute count reduction of phenols on commercial enzymes from 229,226 to 113,352 for overall enzyme dose reductions of approximately 30%. Given the commercial biofuel plant uses 2,327,304 pounds of grain per day and the average human diet is 130 grams of carbohydrate per day, at 453 grams per pound, this is the equivalent to 8.12 million person per year evaluation and with a 10 year experience 81.2 million person years experience with altering polyphenol dosing for carbohydrate metabolism. By extrapolation, by adding 0.5 to 2 grams of polyphenols to the average person daily intake of 1 gram of polyphenol per day, there is postulated a significant reduction in amylolytic (amylase and glucoamylase) activity yielding reduction in carbohydrate metabolism, sugar formation, LDL, glucose, altered gut microbiome, and oxidized lipids. In addition, there will be an increase in nondigestible carbohydrates and altered gastrointestinal microbiome as a consequence.

The administered concentrated oil-based polyphenol composition has an effect on platelet structure and/or function, and/or lipids, and/or inflammatory markers in the patient. A change in platelet structure being meaningful includes changes in pseudopodial development as seen on transmission electron micrographs, or platelet aggregation testing as a measure of platelet function, lipids are measured by meaningful changes in nmr lipid particle size analysis or LDL particle concentration, and inflammatory markers as measured by C-reactive protein (CRP) or high sensitivity CRP.

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A method of administering a concentrated oil-based polyphenol composition to a patient comprising:
   administering a concentrated oil-based polyphenol composition to a patient to treat an ailment, the concentrated oil-based polyphenol composition comprising:
   a polyphenol extracted from a plant material; and
   an oil extracted from the plant material, wherein a concentration is from 500 mg to 3 grams polyphenol(s) in from 0.1 ml to 2 ml oil.

2. The method according to claim 1, wherein the administered concentrated oil-based polyphenol composition has an effect on platelet structure and/or function, and/or lipids, and/or inflammatory markers in the patient.

3. A method of administering a concentrated oil-based polyphenol composition to a patient comprising:
   administering a concentrated oil-based polyphenol composition to a patient to treat an ailment, the concentrated oil-based polyphenol composition comprising:
   a polyphenol extracted from a plant material; and
   an oil extracted from the plant material, wherein a concentration is from 500 mg to 3 grams polyphenol(s) in from 0.1 ml to 2 ml oil, wherein a change in platelet structure being meaningful includes changes in pseudopodial development as seen on transmission electron micrographs, or platelet aggregation testing as a measure of platelet function, lipids are measured by meaningful changes in nmr lipid particle size analysis or LDL particle concentration, and inflammatory markers as measured by C-reactive protein (CRP) or high sensitivity CRP.

4. The method according to claim 1, wherein the concentrated oil-based polyphenol composition comprises a carbohydrate.

5. A method of administering a concentrated oil-based polyphenol composition to a patient comprising:
   administering a concentrated oil-based polyphenol composition to a patient to treat an ailment, the concentrated oil-based polyphenol composition comprising:
   a polyphenol extracted from a plant material; and
   an oil extracted from the plant material, wherein a concentration is from 500 mg to 3 grams polyphenol(s) in from 0.1 ml to 2 ml oil, wherein the administered concentrated oil-based polyphenol composition has an effect on gut microbiome in the patient.

6. The method according to claim 1, wherein the concentrated oil-based polyphenol comprising a mixture of polyphenols.

7. The method according to claim 1, wherein the plant material comprises grain, tree, or cannabis.

8. The method according to claim 1, wherein the concentration is from 500 mg to 3 grams polyphenol(s) in 0.1 ml to 1.5 ml oil.

9. The method according to claim 1, wherein the plant material comprises bagasse from sugar cane or soghum.

* * * * *